United States Patent [19]
Religa et al.

[11] Patent Number: 5,488,789
[45] Date of Patent: Feb. 6, 1996

[54] PROCESS AND APPARATUS FOR THE PRODUCTION OF A HEART VALVE PROSTHESIS

[75] Inventors: Zbigniew Religa, Warsaw; Bogdan Stolarzewicz, Katowice; Romuald Cichon, Bytom; Marek Kryzskow, Swietochlowice; Jolanta Stozek, Katowice, all of Poland

[73] Assignee: Nika Health Products Limited, Vaduz, Liechtenstein

[21] Appl. No.: 146,033
[22] PCT Filed: May 8, 1992
[86] PCT No.: PCT/EP92/01018
§ 371 Date: Jan. 14, 1994
§ 102(e) Date: Jan. 14, 1994
[87] PCT Pub. No.: WO92/19185
PCT Pub. Date: Nov. 12, 1992

[30] Foreign Application Priority Data

May 8, 1991 [EP] European Pat. Off. ............ 91107445

[51] Int. Cl.⁶ ............... D05B 91/10; D05C 1/04; A61F 2/24
[52] U.S. Cl. ............ 38/102.2; 38/102.4; 38/102.91; 623/2; 623/901
[58] Field of Search ............ 112/103; 38/102.91, 38/102.2, 102.4, 102, 102.1; 623/2, 901

[56] References Cited

U.S. PATENT DOCUMENTS

| 437,240 | 9/1890 | Przewdzink | 38/102.2 |
|---|---|---|---|
| 517,860 | 4/1894 | Hooper | 38/102.2 |
| 3,570,014 | 3/1971 | Hancock. | |
| 3,709,175 | 1/1973 | Edwards et al. | 112/262.1 |
| 3,710,744 | 1/1973 | Goodenough et al. | 112/262.1 |
| 3,739,402 | 6/1973 | Cooley et al. . | |
| 3,755,823 | 9/1973 | Hancock . | |
| 4,106,129 | 8/1978 | Carpentier et al. . | |
| 4,451,936 | 6/1984 | Carpentier et al. . | |
| 4,725,274 | 2/1988 | Lane et al. . | |

FOREIGN PATENT DOCUMENTS

| 2700531 | 7/1977 | Germany . | |
|---|---|---|---|
| 54-23632 | 8/1979 | Japan | 38/102.2 |
| WO83/02225 | 7/1983 | WIPO . | |

*Primary Examiner*—David H. Willse
*Attorney, Agent, or Firm*—Oliff & Berridge

[57] ABSTRACT

An elastic textile covering is applied over an annular support of a heart valve prosthesis by inserting the preferably collar shaped textile covering through the annular support, turning two projecting axial ends of the textile covering over the outer surface of the annular support and then joining the two axial ends to each other to form a seam that preferably extends entirely around an outer periphery of the annular support. This seam can be concealed by a collar, which also may be covered by the textile covering. An apparatus for applying the textile covering to the annular support includes two coaxial annular rings into which the annular support and textile covering are inserted. Each of the rings includes structure for attachment to a respective axial end of the textile covering.

9 Claims, 2 Drawing Sheets

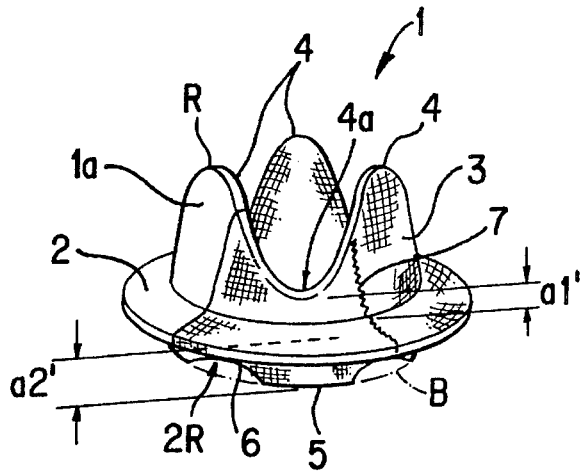
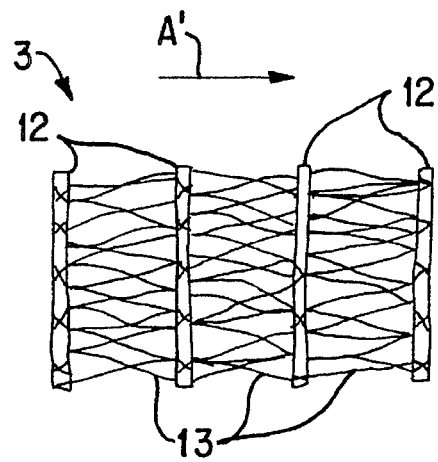
FIG. 1　　　　FIG. 2
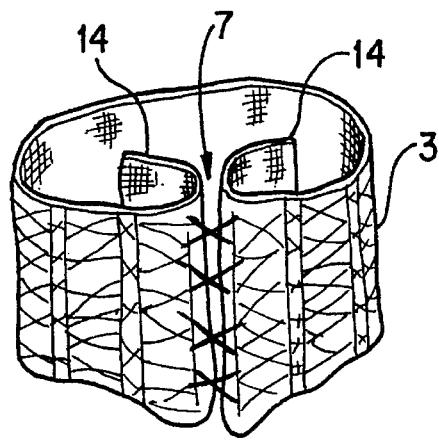
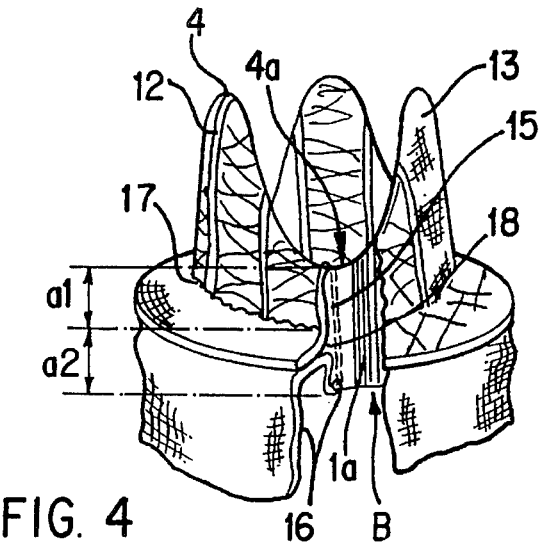
FIG. 3　　　　FIG. 4
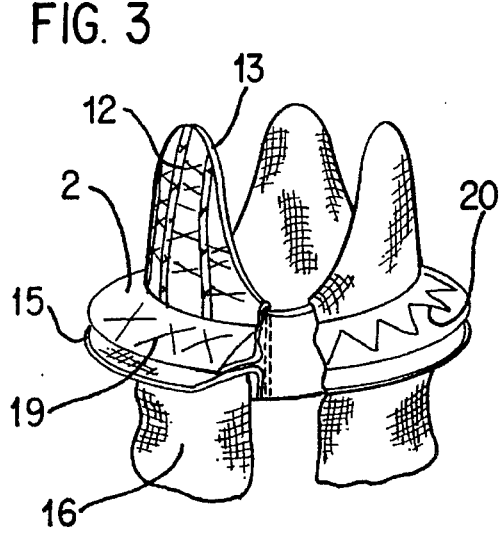
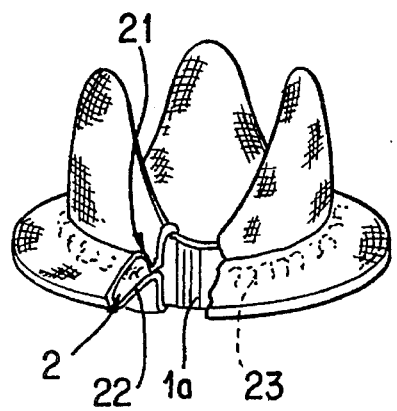
FIG. 5　　　　FIG. 6

PROCESS AND APPARATUS FOR THE PRODUCTION OF A HEART VALVE PROSTHESIS

BACKGROUND OF THE INVENTION

The invention relates to a process for covering an annular support of a heart valve prosthesis with a textile covering, and to an apparatus for carrying out the process.

The known prostheses used in cardiac surgery contain a crown-shaped annular element of plastic, but generally of metal or of both materials. They consist in general of long, often wire-like elements which are predominantly not very elastic and are often joined by soldering or welding. This results in poor adaptability, especially since the joints then become brittle, but in some cases also relatively poor tolerance, not least because the textile covering generally applied to the annular element then requires several seams in order to hold securely on the wire skeleton of the annular element. This results in strength problems and also can make manufacture more difficult. Typical heart valve prostheses of this type are described in U.S. Pat. No. 3,570,014 or U.S. Pat. No. 3,755,823.

SUMMARY OF THE INVENTION

It is the object of the invention to design a heart valve prosthesis of the type described above in such a way that the adaptability and tolerance are improved, strength problems being avoided. This is achieved according to the invention by covering an annular support of a heart valve prosthesis with a textile covering that is elastic at least in one direction. The textile covering is pushed into the annular support and, at its two projecting axial ends, the textile covering is turned over the outer surface of the annular support. The two axial ends of the textile covering then are joined to one another by a seam, which extends around the annular support.

By means of the process according to the invention, the textile covering is mounted on the annular element with a minimum of seams. Thus, on the one hand, the tolerance improves since a plurality of thick seams is avoided but the strength is also improved as a result, since seams always entail a mechanical risk. It would of course also be possible to apply the process according to the invention to conventional annular elements, but it is precisely in combination with a particular, preferred support, disclosed herein, which provides results optimum results.

Although the process according to the invention could also be realised without an apparatus of a particular type, the apparatus according to the invention not only considerably helps and facilitates the implementation of the process and the production of a prosthesis according to the invention but also guarantees uniform quality through the clamping apparatus provided according to the invention. The preferred apparatus for performing this process includes two coaxial rings, which hold the annular support together with the textile covering during assembly. One of the rings includes a fastener for one end of the textile covering. The other ring includes a clamping apparatus for the other end of the textile covering.

BRIEF DESCRIPTION OF THE DRAWINGS

Further details of the invention are evident from the following description of embodiments shown schematically in the drawing.

FIG. 1 shows a heart valve prosthesis according to the invention before attachment of the biological heart valve material;

FIGS. 2 to 6 show the successive steps in carrying out the process according to the invention, starting from a rectangular piece of material according to FIG. 2.

DETAILED DESCRIPTION OF THE PREFERRED EMBODIMENTS

Figure 7:
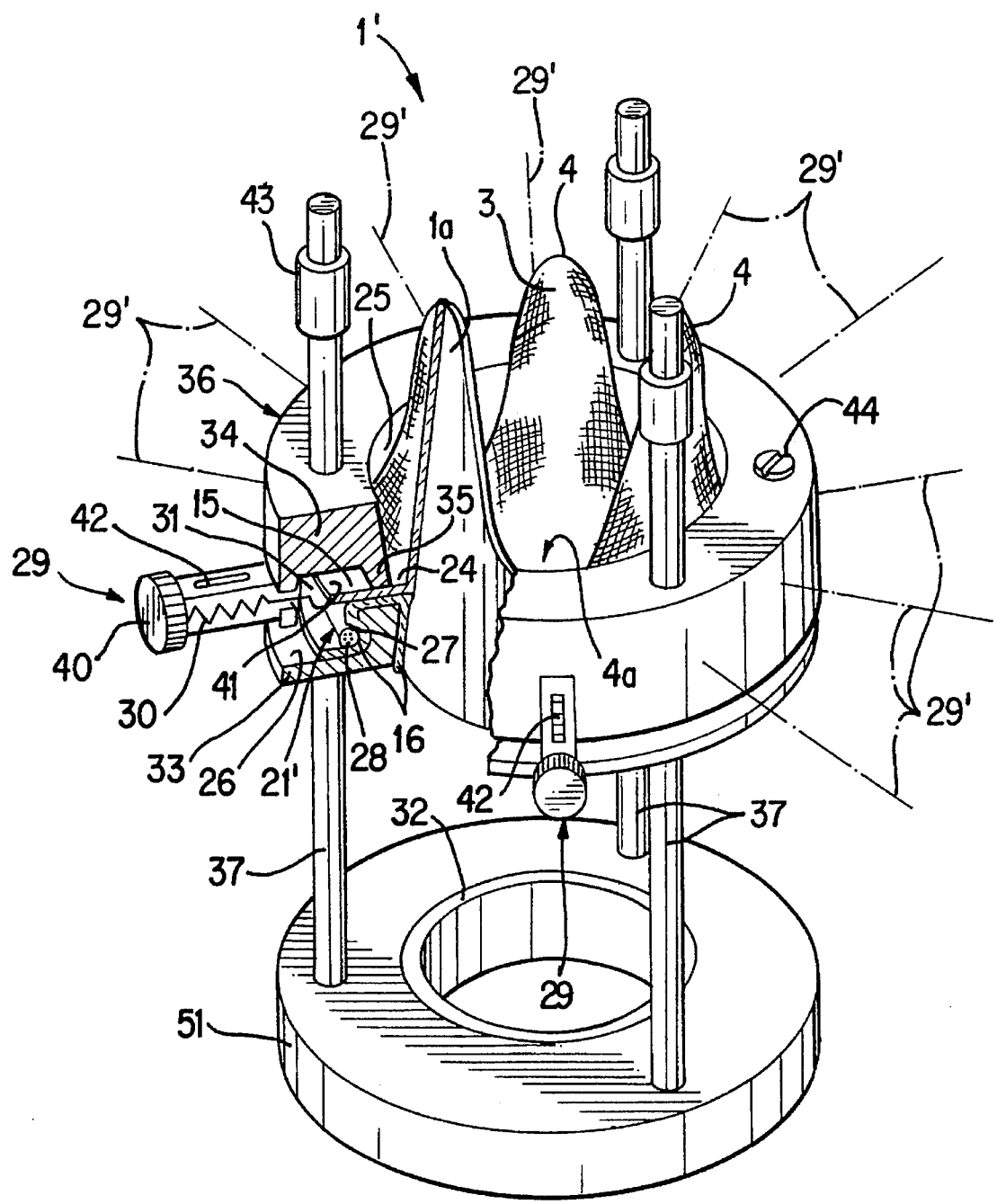
FIG. 7 shows an apparatus according to the invention for carrying out this process.

FIG. 1 shows an oblique view of a heart valve prosthesis 1 according to the invention with partly removed textile covering 3, which covers an annular support 1a together with a collar 2 attached thereto. As can be seen, the annular element 1a consists of flat material, in particular of a thermoplastic, so that it can be produced easily and economically, for example by injection moulding.

The support 1a possesses, in a manner known per se, three axially projecting support arms 4, the free ends of which are rounded. Projections 5 and indentations 6 are arranged alternately on the axial end, the base B, of this support 1a, which end is opposite the support arms 4, it being possible for any excess biological heart valve material which is to be flattened in a conventional manner over the support arms and is to be fastened to the collar 2 to be accommodated in said indentations.

The textile covering 3 is elastic and consists expediently of a network fabric, because such a fabric has sufficient intrinsic elasticity—even when conventional, biologically tolerated textile material is used. In practice, a USCI product, Adavison, from C. R. Bard, Catalogue No. 007831, has proved expedient. This is all the more surprising since nonelastic coverings have been chosen to date; however, it will subsequently become clear that the choice of elastic material results in a simplification in the manufacture of the heart valve prosthesis, improved safety with respect to tearing of seams and a smaller number of such seams, which also improves the tolerance of the prosthesis. This is because in many cases a concealed (and therefore invisible) circumferential seam in the region of the collar 2 will be sufficient, if necessary with a vertical seam 7.

In order to facilitate the process according to the invention—with optimal anatomical fit—it is expedient if the support arms 4 are rounded at their free ends with the radius R which corresponds to not more than one eighth of the diameter of the support 1a in the region of its collar 2. On the other hand, it is advantageous if the indentations 6 are relatively flat, the radius of curvature 2R preferably corresponding to not more than twice the radius of curvature R of the support arms 4. The collar 2 shown in FIG. 1 and consisting of textile or plastic material is expediently mounted between two circumferential lines, of which the upper circumferential line is preferably located a distance a1' of about 1 mm below the base 4a of the support arms 4 but the lower circumferential line is advantageously slightly further away from the edges of the indentations 6, so that a distance a2' of, for example, 2 mm results.

In this context, it is therefore possible first to prefabricate annular elements 1a of different diameters, preferably from 17 mm to 33 mm at the base B. In order thereafter to form a heart valve prosthesis shown in FIG. 1 therefrom, it is necessary to provide—in the manner described, a textile covering 3, which state had to be produced from several individual parts, tediously and with several seams. It is therefore intended, with reference to FIGS. 2 to 6, to describe the process according to the invention, in which, starting from a piece of material closed in a collar-like manner, a single seam is sufficient.

According to FIG. 2, however, a prepared textile collar is not available and must first be produced from a rectangular piece of material in the manner shown. This piece of material consists of a network fabric, for example a knitted fabric, having a sequence of relatively dense strips 12 formed from warp threads and sparser meshes 13 in between, which in particular give the textile covering 3 elasticity in the direction of the arrow A' whereas it has slightly less elasticity in the direction at right angles thereto. A similar material has been put on the market by USCI, Adavison, from C. R. Bard, U.S.A., under Catalogue No. 007831.

Whereas to date nonelastic coverings were used in spite of the large number of seams required, the elasticity of the textile covering 3 used according to the invention allows the latter to be pulled over the support arms 4 and their base region 4a, differences in length being elastically compensated. Of course, the covering 3 consists of medically or biologically tolerated textile material known per se.

Thus, in order to obtain the required collar form according to FIG. 3, the rectangular piece of material according to FIG. 2 is bent with its ends towards one another, and the ends are then connected to one another by a vertical seam 7 (cf. FIG. 1). As can be seen, it is preferable if the edges 14 of the material are provided with a bead in order to increase the strength of the seam 7. To avoid outward-projecting material residues in the covered support 1a, the collar with its bead on the inside according to FIG. 3 is expediently turned outwards before being pulled into the support 1a.

The collar-like fabric sleeve thus formed is pulled through the annular element 1a from the inside according to FIG. 4, so that the collar 2 is coaxial with said annular element and the axial ends of the textile covering project above and below the annular element. From this explanation, it is of course clear that FIG. 3 merely shows a section of the collar, which— in order to be able to project above the support 1a and below the latter—must have a diameter which is substantially smaller than the length of the collar 3.

In any case, the upper projecting end 15 of the covering 3 can thus be turned outwards and downwards in the manner shown in FIG. 4, whereas the lower projecting end 16 is turned outwards from the bottom. If a collar 2 (FIG. 1) is to be mounted, it is expedient if the lower end 16 is chosen to be slightly longer than the upper end 15, since it is intended to be used for covering the collar 2. It is of course also clear that FIG. 4 shows the covering 3 in a partially cut away view with the central strip omitted, since the collar 3 according to FIG. 3 does in fact form a closed hollow cylinder. This section view according to FIG. 4 is merely intended to illustrate the path of the two ends 15 and 16.

As soon as the two ends 15, 16 have been turned into the position shown in FIG. 4, all that is still required is a circumferential seam 17 to sew together the joining points 18 of the two ends 15, 16, which joining points have been pulled together. Seam 17 is located a distance a1 from the base 4a of the support arms 4, and a distance a2 from the base B of annular support 1a. If the starting material used was already a collar-shaped fabric, for example a hollow network article, the seam 17 is the only seam required for the covering and, when a collar 2 is mounted, even this seam is covered by said collar. Instead of a hollow network article, it is also possible to use hollow knitted fabric, network material being preferred because it has intrinsic elasticity which is due to the method of production and is not associated with the use of an elastic material, although such a material could also be used within the scope of the invention, provided it is biologically tolerated. As is evident and is confirmed in practice, this intrinsic elasticity above all compensates any difference in length which, in the case of the support arms 4 with their base area 4a in between, is particularly large. Nevertheless, there is no danger of overstretching of the fabric 3, and the direction of extension along arrow A' of FIG. 2 has proved in practice to be more advantageous than the reverse direction.

Once this point of the process has been reached, it is still necessary to place a plastic piece or the like which forms a collar 2, and has a cross-section which is angular, for example rectangular, but according to FIG. 5 in this case triangular, on the projecting and the short end. 15. It may be advantageous to fasten the collar 2 with the aid of a few cross stitches 19 or zig-zag stitches 20 to the annular element 1a in order to prevent slipping or twisting and for this purpose small through-holes (not shown) may be made in the support 1a, in particular in the region of the upper circumferential line (cf. the upper limit of the collar 2), but in any case along the lower circumferential line (that is to say at the lower limit of the collar 2 or between these lines) in order to facilitate this connection.

The lower, longer end 16 is now folded over the upper surface of the collar 2 (FIG. 6) and around the inner lateral surface of said collar in such a way that the latter is covered by a section 21 and the former by a section 22. This is of course only necessary when the collar 2 is not itself formed from textile material or covering by the textile covering 3 is desired for other reasons, said covering also being used for anchoring in the biological tissue. The turning over of the end section 21 makes it possible to conceal this end and to fasten it to the covering or, if necessary, also to the annular element 1a with the aid of a concealed seam 23, for which purpose the above-mentioned, very small through-holes arranged in the region of the circumferential lines determined by the collar 2 may be used.

By applying the concealed seam 23 in the region of the previously applied seam 17 (FIG. 4), both seams are covered by the collar 2 in such a way than, on the one hand, they are virtually completely invisible from the outside or merge to form a single seam. However, this seam 23 can of course also help to fasten the two end sections 15, 16 (FIG. 4), so that the seam 17 may be in the form of a relatively loose quilting seam. In the final analysis, the appearance of the heart valve prosthesis 1 shown in FIG. 1 is then achieved.

To be able to carry out the process described above in a simplified manner, it is preferable to provide an apparatus according to FIG. 7. This has essentially two rings 33, 34, the internal diameter of which is sufficiently large to hold a complete prosthesis 1', that is to say a prosthesis 1' formed from support 1a and textile covering 3. A certain additional play between the outer diameter of the annular element 1a reinforced with the covering 3 and the internal diameter of the rings 33, 34 makes it possible to apply an all-round seam at a point 24 within the internal diameter of the rings 33, 34, as will be explained below.

First, however, the annular element 1a, with collar 3 inserted through from the inside, is placed in the inner opening 25 of the rings 33, 34. Thereafter, the lower end 16 is then expediently turned outwards over the outer surface of the annular element 1a and is fastened carefully to the lower ring 33 so that it rests with its end section 21', in each case with the same length over the entire circumference, on a support surface 26 of the ring 33. In this position, the lower end 16 is detachably fixed, for example with the aid of a clamping ring 28. This clamping ring can be in the form of a spring ring or in the form of a circumferential ring which can be clamped, for example, with the aid of a toggle lever apparatus (not shown), the first embodiment being preferred. In order to enlarge the clamping area, it is advantageous if the ring 33 has a circumferential seam 27 including the ring 26 together with the piece of fabric clamped by it.

After the lower end 16 has been fastened to the lower ring 33 in this manner, the upper end can be pulled over the support arms 4 and the regions 4a present in between. The upper end 15 is then fastened to the clamping apparatuses 29, which for this purpose are equipped with gripping elements 41, for example with hooks (as shown), but if necessary also with forceps-like grippers. These gripping elements 41 are connected to tension elements, such as springs 30, and are subjected to a lead by these, it being advantageous if the spring force is adjustable with the aid of an adjusting screw 40 in order to be able to adapt it to different prosthesis sizes. On the other hand, adaptation may also be necessary when different coverings are used, since it will generally be necessary also to change the rings 33, 34 when the size of the prostheses 1' is changed, unless the diameter is adjusted by inserting a suitable sleeve into each of the rings 33, 34, which is also possible within the scope of the invention.

Furthermore, the section through the rings 33, 34 shows that the inner surfaces thereof are preferably inclined towards the clamping point at which the ends 15, 16 meet one another, in order to improve the accessibility during sewing. To return to the clamping apparatuses 29, it may be mentioned that it is advantageous if the particular clamping force set can be read on a scale 42 connected to the adjusting screw 40. In order to distribute the clamping force as uniformly as possible over the circumference of the ring 34, a plurality of clamping apparatuses 29, which is indicated merely by their axes 29', is expediently distributed over the circumference of this ring. In order to support these clamping apparatuses 29 on the outside of the ring 34, the latter consists of an inner ring section 35 and an outer ring section 36 on which the clamping apparatuses 29 are fastened. This results in a cavity 31 between the two ring sections 35, 36, in which cavity, as shown, the gripping elements 41 are housed.

Of course, FIG. 7 merely illustrates a preferred embodiment and it would be quite possible to modify the ring 34 so that the gripping means 41 are also readily accessible when rings 33, 34 are placed together, in which case it would also be possible to apply the seam 17 (cf. FIG. 4) not inside the opening 25 but instead just on the outside of the inner ring section 35, in other words where the cavity 31 is located in FIG. 7. However, this requires that, after the rings 33, 34 have been slackened, the textile covering is placed around the annular element 1a under less tension than when the seam is applied, in other words the fabric would have to be more greatly stretched during sewing, which on the one hand would make measurement of the clamping force with the aid of the clamping apparatuses more difficult (where these can be provided at all) and on the other hand would give rise to the danger of overextension of the textile covering 3.

An apparatus as shown in FIG. 7 could also be used for applying a different type of seam connection if, for example, one of the two rings 33, 34 or both rings 33, 34 are equipped with a heatable ring region, thus permitting heat bonding or welding of the two fabric ends 15, 16. However, a weld seam or bonded seam, the production of which is generally simpler, is generally thicker and especially less elastic than a sewn seam, which is therefore preferable for heart prostheses of this type.

In order to hold the rings 33, 34 securely during the operations described above, it is expedient to provide a stand 51 which—for holding the support 1a at the desired working height—is advantageously provided with a retaining bush 32 which is adjustable in height and can be screwed to various depths into the stand 51.

The rings 33, 34, which are held in the indicated clamping position by corresponding clamping means, such as clamping screws 44 or clamps, during application of the seam 17 (FIG. 4), are expediently guided on the stand 51 with the aid of guide columns 37 but can be secured on the latter in the position lowered towards the retaining bush 32 with the aid of adjusting rings 43 which can be moved along the columns 37 and clamped to said columns or with the aid of other blocking elements. After application of the seam 17 inside the opening 25, the collar 2 can be mounted according to FIG. 5, after which the projecting end 15 is cut off.

In practice, either a human (if desired also animal) pulmonary or aortic valve is stored in a nutrient solution (together with antibiotics and other substances) and is sewn to the prosthesis described shortly before use, or the already assembled components of the prosthesis are stored or frozen together in a nutrient solution until they are required. This also enables a high cell survival rate to be achieved, and the prostheses produced in this manner can be used in four different positions.

It should be mentioned that the positioning rings 43 constitute an additional element for holding the rings in the lower position in their mutual clamping position and thus, if necessary, facilitating subsequent pulling of the covering 3. Only when the fabric has been pulled uniformly over the annular element 1a and the meshes run straight along the generatrices of the slightly conical ring 1a is it expedient to effect the final clamping by means of the screws 44.

A large number of modifications are possible within the scope of the invention; thus, the function of the rings 33, 34 could be interchanged with one another by, for example, providing the fastening 27, 28 on the upper ring 34 and the clamping apparatus 29 on the lower ring.

We claim:

1. Apparatus for covering an annular support of a heart valve prosthesis with an elastic textile covering, said apparatus comprising: two coaxial rings having a central opening for holding the annular support together with the covering, a first one of said two coaxial rings having a fastening means for engagement with one end of the textile covering; and a second one of said two coaxial rings having a clamping device for engagement with the other end of the textile covering; a stand attached to the first and second rings for holding the first and second rings in a predetermined position, said stand including guide columns slidably attached to said first and second rings for permitting said first and second rings to be moved along said guide columns while maintaining a relative position between said first and second rings.

2. The apparatus according to claim 1, wherein the opening of the first and second rings has dimensions larger than a diameter of said annular support so that a seam can be applied to the textile covering around the annular support inserted in said opening.

3. The apparatus according to claim 1, wherein the clamping device comprises a plurality of clamping elements distributed over a circumference of the second ring, each of said clamping elements being provided with a gripping element for gripping the textile covering.

4. The apparatus according to claim 3, wherein each of said gripping elements is a hook.

5. The apparatus according to claim 1, further comprising an adjusting means for adjusting the clamping force applied to the textile covering.

6. The apparatus according to claim 5, wherein said adjusting means includes a spring.

7. The apparatus according to claim 1, further comprising at least one ring clamping means for holding the first and second rings in a position clamping the textile covering.

8. The apparatus according to claim 1, further comprising an indicating means for indicating the clamping force applied to the textile covering.

9. The apparatus according to claim 1, wherein said stand includes a supporting base that is adjustable in height for holding the first and second rings at a desired height.

\* \* \* \* \*